US005969181A

United States Patent [19]

Breitenbach et al.

[11] Patent Number: 5,969,181

[45] Date of Patent: Oct. 19, 1999

[54] PREPARATION OF SALTS OF PHARMACEUTICAL ACTIVE SUBSTANCES WHICH HAVE ACIDIC GROUPS

[76] Inventors: Jörg Breitenbach, Hans-Sachs-Ring 11, 68199 Mannheim; Joerg Rosenberg, Bruchstr.29, 67158 Ellerstadt; Jörg Neumann, Paul-Münch-Strasse 12, 67117 Limburgerhof; Jürgen Zeidler, Pfalzring 90; Dirk Simon, Birkenstr. 13, both of 67112 Mutterstadt; Ralph Diener, Raingasse 2a, 67157 Wachenheim, all of Germany

[21] Appl. No.: 08/871,943

[22] Filed: Jun. 10, 1997

[30] Foreign Application Priority Data

Jun. 20, 1996 [DE] Germany .......................... 196 24 607

[51] Int. Cl.[6] .................................................... C07C 53/34

[52] U.S. Cl. ............................................................ 562/496

[58] Field of Search .............................................. 562/496

[56] References Cited

U.S. PATENT DOCUMENTS 4,060,535 11/1977 Cinco ..................................... 562/496

FOREIGN PATENT DOCUMENTS 238 240 9/1987 European Pat. Off. .

*Primary Examiner*—Paul J. Killos

[57] ABSTRACT

A process for preparing salts of pharmaceutical active substances which have acidic groups by reacting the carboxylic acids with a base in the melt, wherein the acids are reacted with at least the stoichiometric amount of a base in an extruder.

6 Claims, No Drawings

PREPARATION OF SALTS OF PHARMACEUTICAL ACTIVE SUBSTANCES WHICH HAVE ACIDIC GROUPS

The present invention relates to a process for preparing salts of pharmaceutical active substances which have acidic groups.

EP-A 238 240 discloses a process in which the acidic form of pesticide active substances is reacted continuously with a Brönsted base in an extruder to give salts of the active substances. Bases mentioned as suitable are alkali metal hydroxides, alkaline earth metal hydroxides, ammonia and amines.

However, products prepared by these known processes still show a marked tendency to absorb moisture from the surrounding air, to form lumps and to deliquesce. In practice, this leads to the problem that the quality, especially the flowability, of these products decreases continuously in containers which have been opened.

It is an object of the present invention to provide a process for preparing salts of pharmaceutical active substances which have acidic groups to result in products which do not have these disadvantageous properties.

We have found that this object is achieved by a process for preparing salts of pharmaceutical active substances which have acidic groups by reacting the acids with a base in the melt, wherein the acids are reacted with at least the stoichiometric amount of a base in an extruder.

The compounds employed according to the invention as pharmaceutical active substances are those having an acidic group, with carboxylic acids or sulfonic acids being preferred.

The process according to the invention is preferably used to prepare salts of derivatives of salicylic acid such as acetylsalicylic acid or of arylcarboxylic acids such as diclofenac, tolmetin or zomepirac. Further preferred carboxylic acids are arylpropylcarboxylic acid derivatives such as ibuprofen, naproxen, fenoprofen, flurbiprofen or ketoprofen or arylacetic acid derivatives such as diclofenac or else indole- and indeneacetic acid derivatives such as indometacin or sulindac. Also suitable are sulfonic acid derivatives such as metamizole.

It is also possible to employ mixtures of active substances.

In place of the optically active acids it is also possible to use their racemates.

It is furthermore possible to combine the carboxylic acids with other active substances, for example with caffeine or codein.

Particularly suitable bases are basic a-amino carboxylic acids, particularly preferably lysine. It is self-evident that the $\alpha$-amino carboxylic acids used as bases are by definition not comprised by the term "pharmaceutical active substances which have acidic groups".

Also suitable as bases are alkali metal or alkaline earth metal bases.

Preferred alkali metal bases and alkaline earth metal bases are acetates which provide free acetic acid in the reaction, and formates which can decompose to water and carbon monoxide, and, in particular, carbonates and bicarbonates (formation of carbon dioxide) of alkaline earth metals and, in particular, of alkali metals, such as sodium acetate, potassium acetate, sodium formate, potassium formate, preferably sodium carbonate, sodium bicarbonate and potassium bicarbonate, very particularly preferably potassium carbonate. Also suitable are mixtures of the abovementioned alkali metal bases and alkaline earth metal bases.

The bases according to the invention are employed in at least the stoichiometric amount, preferably in an excess, in particular in an excess of from 1 to 40, and very particularly preferably from to 30, mol % based on the acids.

Whereas the products resulting with less than the stoichiometric amount of the bases according to the invention would, as a rule, be oily and vary greatly in consistency, the products obtained on use of stoichiometric amounts of the bases according to the invention, and very particularly with an excess, have a granular structure with excellent flow properties and storage stability while being very soluble and dissolving quickly in water.

Volatile substances present in the starting materials and/or produced in the reaction, such as water, carbon dioxide etc., usually escape from the product during the reaction or, if the temperature of the product on emergence from the extruder is sufficiently high, also thereafter.

However, the reaction in an extruder can also be carried out in the presence of an entrainer which assists the escape of the water.

Suitable entrainers are cyclohexane, toluene, petroleum ether, and preferably low molecular weight alcohols, in particular $C_1$-$C_7$-alkanols and $C_1$-$C_7$-alkanediols and, very particularly preferably, primary, secondary and tertiary alcohols such as methanol, ethanol, propanol, isopropanol, n-butanol, isobutanol, tert-butanol, pentanols, hexanols, heptanols and mixtures thereof.

In a preferred embodiment of the process according to the invention, the molten carboxylic acid is reacted in the extruder by intimately mixing with the solid base according to the invention, or the solid acid is introduced into the extruder, where it is melted and reacted with the solid base according to the invention.

The bases according to the invention can also be employed dissolved or suspended in the entrainer.

Solid starting materials can be fed into the extruder as such or in the form of a paste, solution or suspension in a solvent. The solvents to be chosen must be such that their volatilization during the preparation of the extrudates according to the invention is ensured. The abovementioned entrainers are preferably used as solvent.

The starting materials may, depending on their physical properties, initially be mixed before the reaction. Initial mixing of liquid and solid products, for example, has the advantage that the solid substances are wetted beforehand. This generally results in more favorable flow properties of the starting materials.

If flow problems arise during the initial mixing, it is possible to employ flow improvers or antiblocking agents, e.g. calcium carbonate, tricalcium phosphate, colloidal silica gel, micro-crystalline cellulose, starch, sugar alcohols and/or talc. It is also possible to add dyes to the mixtures.

It is furthermore possible for mechanical aids such as vibrators and stirrers to be employed in manipulating the initial mixture.

The type of extruder is immaterial for the process according to the invention. Single screw machines, counterrotating and corotating, intermeshing screw machines and multi-screw extruders are suitable. These devices are familiar to the skilled worker and therefore require no further explanation (compare, for example, EP-A 238 240).

Preferred extruders are corotating, intermeshing screw machines, particularly preferably twin screw extruders.

If the starting materials and/or products are hygroscopic or reactive, the extruder is expediently rendered inert with nitrogen or carbon dioxide before the reaction.

The reaction in the extruder and the subsequent drying of the extrudate can be carried out under atmospheric pressure, under reduced pressure or under elevated pressure at from 0 to 250, in particular from 60 to 150,° C. The reaction time is in the region of 1–5 min.

Depending on the reaction temperature, the product of the reaction in the extruder results in the form of particles or of a plastic composition which can be extruded in a conventional way.

The procedure is preferably such that particles with an average diameter of from 0.1 to 5, preferably from 0.1 to 3, cm are obtained.

The extrudates produced according to the invention can moreover, if volatile substances still adhere to them, be freed of the latter by conventional (drying) processes.

The extrudates produced by the process according to the invention are suitable for direct tabletting, granulating or pelleting. They can also be processed in a subsequent melt extrusion with conventional pharmaceutical ancillary substances.

PREPARATION EXAMPLES

The extrudates were produced by using a corotating, intermeshing twin screw extruder (ZSK 30 from Werner & Pfleiderer, Stuttgart, Germany) which consisted of 8 compartment-like zones which could be heated and cooled separately. These zones are referred to hereinafter as "zone 1", "zone 2" etc., with the starting materials entering at zone 1 and emerging at zone 8. Zone 1 was cooled with water (temperature of the exit water: 38° C). Zone 2 was operated at 80° C., and zones 3 and 4 at 128° C., throughout the test. Zone 4 was furthermore open at the top in order to allow the carbon dioxide and water vapor formed in the reaction to escape. Zones 5, 6, 7 and 8 were cooled with water, with the exit water temperatures being 28° C., 21° C., 21° C. and 20° C. respectively.

Example 1

Preparation of the sodium salt of an ibuprofen racemate 484 g (3.5 mol) of sodium carbonate and 1238 g (6 mol) of ibuprofen were fed each hour by belt weighers equipped with screws at 36 rpm into zone 1 of this extruder. The extruder was operated for 40 hours. The ibuprofen was completely converted into the sodium salt in this test.

The extrudate obtained in this way consisted of coarse-particle granules which were easily soluble in water.

200 mg of the extrudate (particle size 0.5–2 mm) were placed in a USPXXII paddle apparatus for testing the release of active substance. The active substance was completely released within min, and a clear solution formed.

We claim:

1. A process for preparing salts of pharmaceutical active substances which have acidic groups by reacting the carboxylic acids with a base in the melt, wherein the acids are reacted with at least the stoichiometric amount of a base in an extruder.

2. A process as claimed in claim 1, wherein a basic amino acid is employed as base.

3. A process as claimed in claim 1, wherein lysine is employed as base.

4. A process as claimed in claim 1, wherein an alkali metal or alkaline earth metal base is employed as base.

5. A process as claimed in claim 1, wherein an alkali metal or alkaline earth metal base which, under the reaction conditions, decomposes partly or completely to form volatile substances is employed.

6. A process as claimed in claim 1, wherein alkali metal or alkaline earth metal carbonates are employed.

* * * * *